US005681546A

United States Patent [19]

Lee et al.

[11] Patent Number: 5,681,546
[45] Date of Patent: Oct. 28, 1997

[54] HAIR STYLING MOUSSE

[75] Inventors: G. Jae Lee, Trumbull; Frank Jones, Guilford, both of Conn.

[73] Assignee: Chesebrough-Pond's USA Co., Division of Conopco, Inc., Greenwich, Conn.

[21] Appl. No.: 616,983

[22] Filed: Mar. 18, 1996

[51] Int. Cl.$^6$ .................................................. A61K 7/11
[52] U.S. Cl. ..................... 424/45; 424/47; 424/70.11; 424/70.21; 424/70.22; 424/70.27; 424/DIG. 1; 424/DIG. 2; 514/77; 514/937; 514/945; 514/975
[58] Field of Search .................... 424/45, 47, 70.11, 424/70.21, 70.22, 70.27, DIG. 1, DIG. 2; 514/937, 945, 975, 77

[56] References Cited

U.S. PATENT DOCUMENTS

| | | | |
|---|---|---|---|
| 4,595,522 | 6/1986 | Barlett et al. | 424/45 |
| 4,983,383 | 1/1991 | Maksimoski et al. | 424/70.11 |
| 5,002,680 | 3/1991 | Schmidt et al. | 252/90 |
| 5,266,308 | 11/1993 | Lee et al. | 424/70.11 |
| 5,429,815 | 7/1995 | Faryniarz et al. | 424/47 |
| 5,443,817 | 8/1995 | Zimmerman et al. | 424/47 |

FOREIGN PATENT DOCUMENTS

| | | |
|---|---|---|
| 0 686 386 | 12/1995 | European Pat. Off. . |
| 08787 | 5/1993 | WIPO . |
| 95/13788 | 5/1995 | WIPO . |

*Primary Examiner*—Raj Bawa
*Attorney, Agent, or Firm*—Milton L. Honig

[57] ABSTRACT

Hair styling mousse compositions are provided based on a combination of water soluble film-forming resin, an amphoteric surfactant and a propellant system. The system requires a combination of $C_3$–$C_5$ alkane hydrocarbon and dimethyl ether in a respective weight ratio from 4:1 to 1:2.

6 Claims, No Drawings

HAIR STYLING MOUSSE

BACKGROUND OF THE INVENTION

1. Field of the Invention

The invention relates to a foaming hair care composition to achieve styling with improved sensory attributes.

2. The Related Art

Hairspray compositions must meet a number of functional requirements. These include good holding ability and curl retention without giving a harsh, brittle feeling to the hair. Even under humid conditions there must be good hold and curl retention. Another requirement is that the hairspray be capable of being removed upon washing the hair at the time of shampooing. Additionally, the compositions must include the properties of low stickiness, good combing characteristics and a lack of powdering or flaking.

Attainment of these properties is difficult when consideration must be given to good sprayability. All the right characteristics may be found in the hair care concentrate but the propellant system may interfere with delivery. This is particularly sensitive when developing a low organic volatile system required by environmental laws.

U.S. Pat. No. 5,266,308 (Lee et al.) attempts to solve the problem through use of a water soluble vinyl resin in combination with a water-insoluble polyester. Dimethyl ether is the stated preferred propellant. U.S. Pat. No. 5,429,815 (Faryniarz et al.) reports achieving a clear, single-phase self-foaming cleanser through dependence on a propellant system comprising dimethyl ether and volatile hydrocarbon. Hair care resins are not part of these compositions.

Propellant systems based on dimethyl ether, monochlorodifluoromethane and a hydrocarbon are the subject of U.S. Pat. No. 4,595,522 (Bartlett et al.). This three component propellant is reported to have the beneficial property of varying little in vapor pressure over a wide range of compositions. U.S. Pat. No. 5,002,680 (Schmidt et al.) describes mild skin-cleansing aerosol mousse-forming emulsions. Suggested as propellants for these emulsions are hydrocarbon, hydrocarbon mixtures (e.g. "A46" containing butane, isobutane and propane) halohydrocarbons and dimethyl ether.

While there has been considerable progress in the art of developing hair care concentrates and propellants, there remains a need for more progress in these areas.

Accordingly, it is an object of the present invention to provide a hair styling mousse which provides a creamy, velvety foam and imparts stylability to the hair.

It is another object of the present invention to provide a hair styling mousse composition with not only good foaming properties but also that avoids traditional sensory negatives such as sticky feel on the hair.

Still a further object of the present invention is to provide a hair styling mousse composition that dries fairly quickly and does not impart wetness to hair or scalp.

These and other objects of the present invention will become more evident from the following summary and detailed description.

SUMMARY OF THE INVENTION

A hair styling mousse composition is provided including:

(i) from 0.5 to 10% by weight of a water-soluble film-forming resin;

(ii) from 0.1 to 20% by weight of an amphoteric surfactant; and (iii) from 0.5 to 10% of a propellant including a mixture of at least one hydrocarbon and a di($C_1$–$C_4$ alkyl) ether in a weight ratio from 10:1 to 1:4.

DETAILED DESCRIPTION OF THE INVENTION

Now it has been discovered that the objects of this invention can be achieved through use of a critical mixture of propellants in combination with a water soluble film-forming resin and an amphoteric surfactant.

Essential to the present invention is a mixed propellant system of hydrocarbon and dialkyl ether. The dialkyl ether is a di($C_1$–$C_4$ alkyl) ether, most preferably dimethyl ether. The hydrocarbon component of the propellant system will be a $C_3$–$C_5$ alkane, especially one selected from propane, isobutane, n-butane and mixtures thereof. Particularly preferred are combinations of propane and isobutane, known as A50 propellant commercially available from the Aeropress Corporation. Total amount of propellant will range from 0.5 to 10%, preferably from 1.5 to 8%, optimally from 6 to 7.5% by weight. Weight ratios of total hydrocarbon to dialkyl ether will range from 10:1 to 1:4, preferably from 4:1 to 1:2, more preferably from 2:1 to 1:1, optimally 1.5:1 to 1.2:1 by weight.

A second important element of compositions according to the present invention is that of a water soluble film-forming resin. The resin may be either nonionic, anionic, cationic or amphoteric.

Illustrative nonionic resins include polyvinylpyrrolidone (PVP), copolymers of (PVP) and methylmethacrylate, copolymers of PVP and vinyl acetate (VA), polyvinyl alcohol (PVA), copolymers of PVA and crotonic acid, copolymers of PVA and maleic anhydride, hydroxypropyl cellulose, hydroxypropyl guar gum, PVP/ethylmethacrylate/methacrylic acid terpolymer, vinyl acetate/crotonic acid/vinyl neodecanoate copolymer, octylacrylamide/acrylates copolymer, monoethyl ester of poly(methyl vinyl ether/maleic acid) and mixtures thereof.

Illustrative anionic resins are sodium polysytrene sulfonate and any of the aforementioned nonionic resins containing a carboxylic acid group that has been neutralized with a base. For example, the anionic resins would include a partially or fully neutralized triethanolamine salt of PVA/crotonic acid.

Illustrative cationic resins include quaternized cellulose ethers such as Polyquaternium 10 (hydroxyethylcellulose hydroxypropyl trimethylammonium chloride ether) under the trade name Ucare Polymer LR and Polyquaternium 4 (hydroxyethylcellulose dimethyldiallyl ammonium chloride copolymer) under the trade name Celquat, quaternized vinyl pyrrolidone/alkylaminoacrylate or methacrylate copolymers such as dimethyl sulfate salt under the trade name Gafquat; methylvinylimidazolium vinylpyrrolidone; octylacrylamide acrylate butylaminoethyl methacrylate copolymers; N-methacryloyl ethyl-N,N'-dimethyl ammonium gamma-N-methyl carboxy betaine butyl methacrylate copolymer under the trade name Yukaformer AM-75, and mixtures thereof.

Amounts of these film-forming resins may range from 0.5 to 10%, preferably from 1 to 8%, optimally from 1.5 to 4% by weight.

Another important element of compositions according to the present invention is that of an amphoteric surfactant. Suitable examples include $C_8$–$C_{18}$ alkyl imidazoline derivatives having either one or two carboxylic acid groups substituted onto the nitrogen atom in the 1 position of the imidazoliyl ring; the $C_8$–$C_{18}$ alkyl amino alkyl substituted betaines; the $C_8$–$C_{18}$ amino sulphonates; the sulfonated $C_8$–$C_{18}$ alkyl amines; alkyl carboxyglycinates; acyl glutamates and the N-alkyl-β-aminopropionic acids, wherein the alkyl is a $C_8$–$C_{18}$ group. Most preferred is cocamidopropyl betaine, commercially available as Tegobetaine F® from the Goldschmidt Company. Amounts of the amphoteric surfactant will range from 0.1 to 20%, preferably from 0.5 to 3%, optimally between 0.6 and 1% by weight.

Compositions of this invention advantageously can include hair conditioning agents. Most preferred is phytantriol. Phytantriol as known by its CTFA name is a hydrophobic branched triol chemically identified as 3,7,11,15-tetramethyl-1,2,3-hexadecanetriol. Commercially it is available from Hoffmann-La Roche, Inc., Nutley, N.J. For purposes of the present invention, the amount of phytantriol will range from 0.001 to 1%, preferably from 0.01 to 0.5%, optimally from 0.05 to 0.2% by weight.

Silicone compounds may be chosen from volatile and non-volatile silicone fluids. Volatile silicone fluids are preferably oils chosen from cyclic or linear polydimethyl siloxanes containing from 3 to 9, preferably from 4 to 5 silicon atoms.

Cyclomethicone is the most preferred cyclic volatile silicone. Linear volatile silicone oils generally have viscosities less than about 5 centistokes at 25° C. while cyclic fluids typically have viscosities of less than about 10 centistokes.

Nonvolatile silicone oils useful for the present invention include polyalkyl siloxanes, polyalkylaryl siloxanes and polyether siloxane copolymers. Non-volatile polyalkyl siloxanes useful herein include, for example, polydimethyl siloxanes with viscosities of from 5 to 100,000 centistokes at 25° C. Among the preferred non-volatile silicones are the polydimethyl siloxanes having viscosities from 10 to 400 centistokes at 25° C. These siloxanes are available, for example, from the General Electric Company as SF 1075 methyl phenyl fluid or from Dow Corning as 556 Cosmetic Grade Fluid.

The non-volatile polyalkylaryl siloxane fluids that may be used include, for example, polymethylphenylsiloxanes having viscosities of about 15 to 30,000 centistokes at 25° C.

Also includable are minor amounts of other ingredients commonly found in hair care compositions, such as preservatives, keratin amino acids, UV inhibitors, fragrances, coloring agents, buffering agents, polyols and other moisturizing agents.

Water will be present in compositions of the present invention. Amounts may range from 50 to 99%, preferably from 85 to 96% by weight.

The following examples will illustrate preferred embodiments within the scope of the present invention. These examples are solely for the purpose of illustration and are not to be construed as limitations of the present invention as many variations thereof are possible without departing from the purview and spirit of the invention.

EXAMPLE 1

A hair styling mousse according to the present invention was prepared according to the formulation described below.

TABLE I

| INGREDIENT | WEIGHT % |
|---|---|
| Concentrate | 93.00 |
| Polyquaternium-4 | 2.00 |
| Tegobetaine F (Cocamidopropyl Betaine) | 0.70 |
| Glydant Plus (DMDM Hydantoin) | 0.05 |

TABLE I-continued

| INGREDIENT | WEIGHT % |
|---|---|
| Crotein HKP (Hair Keratin Amino Acids) | 0.25 |
| Cyclomethicone | 0.25 |
| Phytantriol (3,7,11,15-tetramethyl-1,2,3-hexadecanetriol) | 0.10 |
| Fragrance | 0.20 |
| Water | balance |
| Propellant | 7.00 |
| A50 Propellant (16% Propane/84% Isobutane) | 4.20 |
| Dimethyl Ether | 2.80 |

EXAMPLE 2

The effect of the propellant mixture was evaluated by an expert panel. The concentrate was divided into two sample groups and each were filled into aluminum pressure cans. A50 propellant (16% propane/84% isobutane) was charged into cans of the first group. A 60:40 mixture of A50 and dimethyl ether was charged into the cans of the second group. Each group of cans was loaded with a ratio of 93:7 of concentrate to propellant.

Charged samples were brought to room temperature by placing them on a laboratory bench overnight. Before dispensing, each can was hand held and shaken 5 times in an up and down motion travelling 15–18 inches each time. Then a sample of mousse was dispensed onto the palm of an evaluator's hand by depressing the foam nozzle actuator on each of the cans for 3 seconds. Foam was rubbed and worked into both hands for 5 seconds. It was then applied onto a medium length brown hair dummy's head.

Sensory properites of the foam were evaluated for creaminess, softness, dry/wet feel, spreadability and sticky feel by the expert panelists.

TABLE II

| | PROPELLANT | |
|---|---|---|
| | A50 | A50/DME(60-40) |
| Creaminess | Good | Excellent |
| Softness | Fair | Excellent |
| Dry/Wet | Dry | Just Right (balanced between wet/dry) |
| Spreadability | Good | V. Good |
| Sticky Feel | Good | V. Good |

Evident from the results of the panel evaluation is that best performance was obtained through a combination of hydrocarbon and dimethyl ether.

EXAMPLE 3

An In-Home Use Test was conducted with 40–50 participants per test sample. The participants were females ranging from 18 to 34 years in age. They were regular mousse users at least 3–4 times per week. Each was requested to replace their regular mousse for two weeks with the test sample. Forty-four participants were given the Example 1 mousse (with A50/DME propellant blend) while a second group of 52 participants were sampled with the same concentrate except the propellant was exclusively A50 hydrocarbon. The results are recorded in Table III.

TABLE III

ATTRIBUTE MEAN SCORES

| | A50/DME PROPELLANT BLEND N = 44 | A50 HYDROCARBON PROPELLANT N = 52 |
|---|---|---|
| Applying Evenly | 4.3 | 4.0 |
| Holds Hair Style | 4.1* | 3.6 |
| Not Causing Flaking | 4.4 | 4.1 |
| Leaves Hair Soft | 4.2 | 4.0 |
| Drying Quickly | 4.3* | 3.9 |
| Not Feeling Sticky | 4.3* | 3.9 |
| Adds Body/Fullness | 4.2 | 3.8 |
| Easy to Style | 4.2* | 3.8 |
| Applying Easily | 4.4 | 4.2 |
| Leaves Hair Manageable | 4.3* | 3.9 |
| Prevents Fly-Away | 4.1 | 3.8 |
| Ease of Combing | 4.2 | 4.1 |
| Pleasant Fragrance | 4.0 | 4.0 |
| Leaves Natural Shine | 4.0 | 3.8 |
| Easily Washed Out | 4.4 | 4.0 |
| Not Feeling Coated | 4.2 | 4.0 |
| Not Looking Dull | 4.3 | 4.0 |
| Hair Feels Silky | 3.9 | 3.8 |
| Looks Healthy | 4.2 | 3.9 |
| Mean Average | 4.2 | 3.9 |

5 = Excellent
1 = Poor
*Propellant Blend Significantly Better Than A50 alone.

The propellant blend of hydrocarbon and dimethylether was significantly better on attribute mean scores in all categories. It was also significantly better than the hydrocarbon propellant on the attributes of holds hair style, drying quickly, not feeling sticky, easy to style and leaves hair manageable.

EXAMPLE 4

Another illustrative formulation according to the present invention is described below.

TABLE IV

| INGREDIENT | WEIGHT % |
|---|---|
| Concentrate | 93.00 |
| Polyquaternium-4 | 3.00 |
| Tegobetaine F (Cocamidopropyl Betaine) | 0.70 |
| Glydant Plus (DMDM Hydantoin) | 0.05 |
| Crotein HKP (Hair Keratin Amino Acids) | 0.25 |
| Cyclomethicone | 0.10 |
| Phytantriol (3,7,11,15-tetramethyl-1,2,3-hexadecanetriol) | 0.025 |
| Fragrance | 0.20 |
| Water | balance |
| Propellant | 7.00 |
| A46 Propellant | 3.50 |
| Dimethyl Ether | 3.50 |

EXAMPLE 5

Another illustrative formulation according to the present invention is described below.

TABLE V

| INGREDIENT | WEIGHT % |
|---|---|
| Concentrate | 96.00 |
| Polyquaternium-4 | 2.00 |
| Tegobetaine F (Cocamidopropyl Betaine) | 0.70 |
| Glydant Plus (DMDM Hydantoin) | 0.05 |
| Crotein HKP (Hair Keratin Amino Acids) | 0.25 |
| Cyclomethicone | 0.25 |
| Phytantriol (3,7,11,15-tetramethyl-1,2,3-hexadecanetriol) | 0.02 |
| Fragrance | 0.20 |
| Water | balance |
| Propellant | 4.00 |
| A50 Propellant | 1.50 |
| Dimethyl Ether | 2.50 |

EXAMPLE 6

Another illustrative formulation according to the present invention is described below.

TABLE VI

| INGREDIENT | WEIGHT % |
|---|---|
| Concentrate | 94.00 |
| Polyquaternium-10 | 2.00 |
| Tegobetaine F (Cocamidopropyl Betaine) | 0.70 |
| Glydant Plus (DMDM Hydantoin) | 0.50 |
| Crotein HKP (Hair Keratin Amino Acids) | 0.25 |
| Cyclomethicone | 0.25 |
| Phytantriol (3,7,11,15-tetramethyl-1,2,3-hexadecanetriol) | 0.25 |
| Fragrance | 0.20 |
| Water | balance |
| Propellant | 6.00 |
| A31 Propellant (100% isobutane) | 3.80 |
| Dimethyl Ether | 2.20 |

EXAMPLE 7

Another illustrative formulation according to the present invention is described below.

TABLE VII

| INGREDIENT | WEIGHT % |
|---|---|
| Concentrate | 93.00 |
| Luviskol PVP/VA | 2.00 |
| Sulfobetaine | 0.70 |
| Glydant Plus (DMDM Hydantoin) | 0.05 |
| Crotein HKP (Hair Keratin Amino Acids) | 0.25 |
| Cyclomethicone | 0.25 |
| Phytantriol (3,7,11,15-tetramethyl-1,2,3-hexadecanetriol) | 0.25 |
| Fragrance | 0.20 |
| Water | balance |
| Propellant | 7.00 |
| A50 Propellant | 4.20 |
| Dimethyl Ether | 2.80 |

EXAMPLE 8

Another illustrative formulation according to the present invention is described below.

TABLE VIII

| INGREDIENT | WEIGHT % |
| --- | --- |
| Concentrate | 93.00 |
| Polyvinylpyrrolidone | 2.00 |
| Tegobetaine F (Cocamidopropyl Betaine) | 0.70 |
| Glydant Plus (DMDM Hydantoin) | 0.05 |
| Crotein HKP (Hair Keratin Amino Acids) | 0.25 |
| Cyclomethicone | 0.10 |
| Phytantriol (3,7,11,15-tetramethyl-1,2,3-hexadecanetriol) | 0.10 |
| Fragrance | 0.20 |
| Water | balance |
| Propellant | 7.00 |
| A46 Propellant | 4.20 |
| Dimethyl Ether | 2.80 |

EXAMPLE 9

Another illustrative formulation according to the present invention is described below.

TABLE IX

| INGREDIENT | WEIGHT % |
| --- | --- |
| Concentrate | 90.00 |
| Poly(Methylvinylimidazolium vinylpyrrolidone) | 2.00 |
| Tegobetaine F (Cocamidopropyl Betaine) | 0.70 |
| Glydant Plus (DMDM Hydantoin) | 0.05 |
| Crotein HKP (Hair Keratin Amino Acids) | 0.25 |
| Cyclomethicone | 0.10 |
| Phytantriol (3,7,11,15-tetramethyl-1,2,3-hexadecanetriol) | 0.10 |
| Fragrance | 0.20 |
| Water | balance |
| Propellant | 10.00 |
| A50 Propellant | 4.20 |
| Dimethyl Ether | 6.80 |

EXAMPLE 10

Another illustrative formulation according to the present invention is described below.

TABLE X

| INGREDIENT | WEIGHT % |
| --- | --- |
| Concentrate | 93.00 |
| Amphomer ® | 4.00 |
| Tegobetaine F (Cocamidopropyl Betaine) | 0.70 |
| Glydant Plus (DMDM Hydantoin) | 0.05 |
| Crotein HKP (Hair Keratin Amino Acids) | 0.25 |
| Cyclomethicone | 0.25 |
| Phytantriol (3,7,11,15-tetramethyl-1,2,3-hexadecanetriol) | 0.05 |
| Fragrance | 0.20 |
| Water | balance |
| Propellant | 7.00 |
| A50 Propellant | 4.20 |
| Dimethyl Ether | 2.80 |

EXAMPLE 11

Another illustrative formulation according to the present invention is described below.

TABLE XI

| INGREDIENT | WEIGHT % |
| --- | --- |
| Concentrate | 93.00 |
| Polyquaternium-4 | 2.00 |
| Tegobetaine F (Cocamidopropyl Betaine) | 0.70 |
| Glydant Plus (DMDM Hydantoin) | 0.05 |
| Crotein HKP (Hair Keratin Amino Acids) | 0.25 |
| Cyclomethicone | 0.10 |
| Phytantriol (3,7,11,15-tetramethyl-1,2,3-hexadecanetriol) | 0.05 |
| Fragrance | 0.20 |
| Water | balance |
| Propellant | 7.00 |
| A46 Propellant | 3.00 |
| Dimethyl Ether | 4.00 |

EXAMPLE 12

Another illustrative formulation according to the present invention is described below.

TABLE XII

| INGREDIENT | WEIGHT % |
| --- | --- |
| Concentrate | 93.00 |
| Polyquaternium-4 | 1.00 |
| Polyvinylpyrrolidone | 1.00 |
| Tegobetaine F (Cocamidopropyl Betaine) | 0.70 |
| Glydant Plus (DMDM Hydantoin) | 0.05 |
| Crotein HKP (Hair Keratin Amino Acids) | 0.25 |
| Cyclomethicone | 0.25 |
| Phytantriol (3,7,11,15-tetramethyl-1,2,3-hexadecanetriol) | 0.01 |
| Fragrance | 0.20 |
| Water | balance |
| Propellant | 7.00 |
| A50 Propellant | 4.20 |
| Dimethyl Ether | 2.80 |

The foregoing description and Examples illustrate selected embodiments of the present invention and in light thereof various modifications will be suggested to one skilled in the art, all of which are within the spirit and purview of this invention.

What is claimed is:

1. A hair styling mousse composition comprising:
   (I) from 0.5 to 10% by weight of a water-soluble film-forming resin;
   (ii) from 0.1 to 20% by weight of an amphoteric betaine surfactant; and
   (iii) from 0.5 to 10% of a propellant comprising a mixture of at least one $C_3$–$C_5$ alkane hydrocarbon and dimethyl ether in a weight ratio from 4:1 to 1:2.

2. The composition according to claim 1 wherein the hydrocarbon is a mixture of propane and isobutane.

3. The composition according to claim 1 wherein the amphoteric surfactant is cocamido propyl betaine.

4. The composition according to claim 1 wherein the water-soluble film-forming resin is selected from cationic, anionic, nonionic and amphoteric polymers.

5. The composition according to claim 1 wherein the water soluble film-forming resin is a cationic cellulosic polymer.

6. The composition according to claim 7 wherein the cationic cellulosic copolymer is a copolymer of hydroxyethyl cellulose and diallyl dimethyl ammonium chloride.

* * * * *